US012808649B2

(12) United States Patent
Clonch et al.

(10) Patent No.: US 12,808,649 B2
(45) **Date of Patent: *Nov. 24, 2026**

(54) MAGNETIC DENDROMETER APPARATUS AND CORRESPONDING METHOD

(71) Applicant: Oregon State University, Corvallis, OR (US)

(72) Inventors: Cameron Clonch, Corvallis, OR (US); Bryson Goto, Corvallis, OR (US); Mark Huynh, Corvallis, OR (US); John Selker, Corvallis, OR (US); Chet Udell, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 252 days.

This patent is subject to a terminal disclaimer.

(21) Appl. No.: 18/744,409

(22) Filed: Jun. 14, 2024

(65) Prior Publication Data

US 2024/0337477 A1 Oct. 10, 2024

Related U.S. Application Data

(63) Continuation of application No. 17/541,151, filed on Dec. 2, 2021, now Pat. No. 12,092,452.

(51) Int. Cl.
*G01B 7/12* (2006.01)
*G01B 5/00* (2006.01)
(Continued)

(52) U.S. Cl.
CPC ............. *G01B 7/12* (2013.01); *G01B 5/0035* (2013.01); *G01B 5/025* (2013.01); *G01N 33/0098* (2013.01)

(58) Field of Classification Search
CPC ........................................................ G01B 7/12
(Continued)

(56) References Cited

U.S. PATENT DOCUMENTS 2,855,687 A * 10/1958 Price ........................ G01B 3/22 33/709
3,727,151 A * 4/1973 Koehler ................. H10N 97/00 368/167
(Continued)

FOREIGN PATENT DOCUMENTS

AU 2002349058 A1 * 5/2004 ............... G01B 7/18

OTHER PUBLICATIONS

"Dendrometers." Edaphic Scientific. https://www.edaphic.com.au/products/Dendrometers/ (accessed Jun. 21, 2020).
(Continued)

*Primary Examiner* — George B Bennett
(74) *Attorney, Agent, or Firm* — MUGHAL GAUDRY & FRANKLIN PC

(57) ABSTRACT

Described herein is a magnetic dendrometer having a frame, a spring-tension mechanism, and a magnet for moving together with the spring-tension mechanism. A magnetic sensor is attached to the frame. The magnetic sensor senses the linear motion of the magnet. This linear motion translates to trackable fluctuations in magnetic field. The magnetic fluctuations are converted to electrical signals by the magnetic sensor. A spring is attached to a free-floating wishbone-style component. The free-floating wishbone-style component is couped to a slider which has an adjustable, single-contact point with a target (e.g., a vine, a branch, etc.). The frame is a stationary frame that carries the magnetic sensor. The frame connected via the spring to the wishbone/slider combination cooperates with each other for providing linear motion to extend or contract the spring in length directions. The length variations of the dendrometer spring are converted to linear motion of the magnet and then into electronic signals.

20 Claims, 12 Drawing Sheets

(51) Int. Cl.
*G01B 5/02* (2006.01)
*G01N 33/00* (2006.01)

(58) Field of Classification Search
USPC .............................................. 33/555.1, 555.3
See application file for complete search history.

(56) References Cited

U.S. PATENT DOCUMENTS

| | | | | |
|---|---|---|---|---|
| 4,290,311 | A | 9/1981 | Brewer | |
| 4,549,355 | A | 10/1985 | Sauer et al. | |
| 5,067,246 | A | 11/1991 | Hesske et al. | |
| 5,774,999 | A | 7/1998 | Smith | |
| 6,009,631 | A | 1/2000 | Gensler | |
| 7,207,230 | B2 | 4/2007 | Smith et al. | |
| 7,398,602 | B2 | 7/2008 | Cohen Amar | |
| 7,795,763 | B2 * | 9/2010 | Harris | H02K 35/02 290/1 R |
| 7,830,142 | B2 * | 11/2010 | Blumberg | G01R 33/028 324/244 |
| 9,377,288 | B2 | 6/2016 | DeLucia et al. | |
| 10,809,240 | B2 | 10/2020 | Afzal | |
| D1,021,580 | S | 4/2024 | Clonch et al. | |
| 12,092,452 | B2 * | 9/2024 | Clonch | G01B 5/025 |
| 12,345,527 | B1 * | 7/2025 | Namdeo | G01B 7/12 |
| 2025/0035565 | A1 * | 1/2025 | Yadav | G01N 22/00 |
| 2026/0133022 | A1 * | 5/2026 | Selker | G01B 5/0035 |

OTHER PUBLICATIONS

"DEX Fruit Dendrometers" ICT International. https://ictinternational.com/products/dex-fruit-dendrometers/dex-fruit-dendrometers/ (accessed Nov. 2021).

"Home of the Point Dendrometers" Natkon. https://natkon.ch/ (accessed Jun. 20, 2020).

AS5311 High Resolution Magnetic Linear Encoder, 13th ed., AMS, Premstaetten, Austria. Available: https://www.mouser.com/datasheet/2/588/AS5311_DS000200_2-00-263458.pdf (33 pages).

Coefficients of Linear Thermal Expansion. Engineering Toolbox. https://www.engineeringtoolbox.com/linear-expansion-coefficients-d_95.html (accessed Dec. 12, 2020).

Conesa, M. et al., "Maximum daily trunk shrinkage and daily stem water potential reference equations for irrigation scheduling in table grapes," in Agricultural Water Management vol. 172(1), pp. 51-61, Jul. 2016. Available: http://dx.doi.org/10.1016/j.agwat.2016.04.011.

Dong, C. et al., "Evaluation of thermal expansion coefficient of carbon fiber reinforced composites using electronic speckle interferometry," Optics Express, vol. 25(1), pp. 531-543 (2018). Available: https://doi.org/10.1364/OE.26.000531.

Fernandez, J. et al., "Irrigation scheduling from stem diameter variations: A review," in Agricultural and Forest Meteorology (Elsevier), vol. 150, Issue 2, Feb. 15, 2010, pp. 135-151. Nov. 2009. [Online]. Available: http://dx.doi.org/10.1016/j.agrformet.2009.11.006.

Gambetta et al., "The physiology of drought stress in grapevine: towards an integrative definition of drought tolerance," Journal of Experimental Botany, vol. 71, Issue 16, Aug. 6, 2020, pp. 4658-4676, https://doi.org/10.1093/jxb/eraa245.

Global Tree Growth Project, "Dendrometer observations of short-term tree growth" Smithsonian Environmental Research Center. https://serc.si.edu/research/projects/global-tree-growth-project (accessed Feb. 19, 2021).

ICT International, Large Stem Point Dendrometer. Available: https://www.ictinternational.com/products/large-stem-point-dendrometer/large-stem-point-dendrometer/ Accessed Nov. 12, 2021, 4 pages.

Intrigliolo, D. et al., "Evaluation of grapevine water status from trunk diameter variations" in Irrigation Science, vol. 26, Issue 1, pp. 49-59, Sep. 2007. [Online]. Available: http://dx.doi.org/10.1007/s00271-007-0071-2.

Levin, A., "Re-evaluating pressure chamber methods of water status determination in field-grown grapevine (*Vitis* spp.)" in Agricultural Water Management vol. 221 pp. 422-429, Jul. 20, 2019. Available: doi: 10.1016/j.agwat.2019.03.026.

Matthews, M. et al., "Dependence of Wine Sensory Attributes on Vine Water Status". 2019. Journal of the Science of Food and Agriculture, vol. Issue 3, pp. 321-335. Available: https://doi.org/10.1002/jsfa.2740510305.

McCutchan, H., et al. "Stem-water Potential as a Sensitive Indicator of Water Stress in Prune Trees (*Prunus domestica* L. cv. French)" in Journal of the American Society for Horticultural Science. vol. 117)4), pp. 607-611 (5 pages). 1992. Available: https://doi.org/10.21273/JASHS.117.4.607v.

Notice of Allowance notified May 1, 2024 for U.S. Appl. No. 17/541,151.

Pearsall, K. et al., "Evaluating the potential of a novel dual heat-pulse sensor to measure volumetric water use in grapevines under a range of flow conditions". 2014. Functional Plant Biology, vol. 41(8), pp. 874-883. Available: doi: 10.1071/FP13156.

Santesteban, L. et al., "Discrimination ability of leaf and stem water potential at different times of the day through a meta-analysis in grapevine (*Vitis vinifera* L.)" in Agricultural Water Management vol. 221, pp. 202-210, Jul. 20, 2019. Available: doi: 10.1016/j.agwat.2019.04.020.

Temnani, A. et al., "Irrigation Protocols in Different Water Availability Scenarios for 'Crimson Seedless' Table Grapes under Mediterranean Semi-Arid Conditions," Water 2021, vol. 13, Issue 1, p. 22. Available: https://dx.doi.org/10.3390/w13010022.

Wang, J. et al., "New Inexpensive Dendrometers for Monitoring Crop Tree Growth" Irrigation Toolbox. Nov. 2008, 24 pages. Available: http://irrigationtoolbox.com/ReferenceDocuments/TechnicalPapers/IA/2008/2124translated.pdf.

Williams, L. et al., "Relationship among Ambient Temperature and Vapor Pressure Deficit and Leaf and Stem Water Potentials of Fully Irrigated, Field-Grown Grapevines" in American Journal of Enology and Viticulture, vol. 58(2), 10 pages. Jun. 2007.

WSL, (28) Point dendrometer. Available: https://www.wsl.ch/en/about-wsl/instrumented-field-sites-and-laboratories/lwf-demonstration-site/20-vegetation-and-biodiversity/28-point-dendrometer.html. Accessed Nov. 12, 2021. 2 pages.

* cited by examiner 500 (e.g. 121)

900

1000

1100

1200

MAGNETIC DENDROMETER APPARATUS AND CORRESPONDING METHOD

STATEMENT OF GOVERNMENT INTEREST

This invention was made with government support under Hatch project NI18HFPXXXXXG055 awarded by USDA National Institute of Food and Agriculture and under 1832170 awarded by National Science Foundation. The Government has certain rights in the invention.

CLAIM FOR PRIORITY

This application claims priority to U.S. Provisional patent application Ser. No. 17/541,151, filed on Dec. 2, 2021, titled “MAGNETIC DENDROMETER APPARATUS AND CORRESPONDING METHOD,” which is incorporated by reference in its entirety for all purposes.

BACKGROUND

Fulfilling agricultural demand for freshwater resources in the face of a changing climate is a challenge that often confronts growers, particularly in regions experiencing drought conditions. Current methods for the acquisition of highly accurate plant water stress data are expensive, discontinuous, and/or inaccessible for users without advanced training. Growers are responsible for irrigation management on their land, but their decisions are influenced, and limited by, the finite availability of water each year. Water scarcity can lead to overwatering in response to expected water deficits; these deficits can significantly reduce plant growth and development, directly impacting crop quantity and quality.

Dendrometers quantify plant stress by continuously measuring stem diameter throughout the day. Plant stem diameter oscillates diurnally through periods of expansion and contraction. These oscillations correlate inversely with stress associated with plant transpiration; e.g., when the plant is well-watered, oscillations will be less pronounced (lower amplitude), whereas when experiencing a water deficit and transpiration is reduced, the oscillations will be more extreme (higher amplitude).

Understanding crop water stress provides valuable information regarding plant development that can assist in optimizing irrigation scheduling. Water scarcity in regions common for fruit production, coupled with an increasing world population, makes the use of precise irrigation techniques in vineyards and orchards essential. Continuous measurement of plant water stress can optimize water application by informing irrigators on precisely when irrigation is needed. Ultimately, this leads to improved productivity and water conservation, sustaining essential agroecosystems and natural ecosystems. This increased robustness can have long-lasting effects on the overall socio-economic well-being of agricultural areas.

Furthermore, plant water deficits correlate to altered, sometimes more desirable, fruit physiology and development. For example, in grapevines (e.g., *Vitis vinifera* L.), targeted water stress can change sugar content, fruit skin characteristics, color, wine aroma, berry size, and more. The timing of this water stress can impact grape and wine quality. Indeed, growers of red wine grapes often purposefully employ water deficits to increase accumulation of certain metabolites and alter the ratio of berry skin to flesh. Active evaluation of plant water stress provides a means for enhanced crop customization and better understanding of plant physiology.

Currently there two types of dendrometers: band and point dendrometers. These two types of dendrometers can also be categorized into linear variable placement transducer (LVDT)- and potentiometer-based sensor measurement methods for evaluating stem diameter changes. Potentiometers are adjustable resistors that rely on having a contact that moves across a resistive element. This motion inherently involves friction between internal parts. LVDT sensors do not have the internal friction-inducing elements that are characteristic of potentiometer, but their performance is sensitive to temperature. Field temperatures typically fluctuate from 10-50° C.; the temperature sensitivity of LVDTs is problematic for data accuracy. Band dendrometers, such as the Model 9605 BEI by Duncan Electronics, and point dendrometers, like the Natkon Dendrometer ZN12-O-WP tend to lack precision and accuracy due to their mechanical design premises. For example, band and point dendrometers encounter a significant amount of friction that leads to inaccurate measurements. Delays from “stickiness” due to seals between sliding parts lead to hysteresis: as the stem switches between expanding and contracting, the instrument is unable to measure and record these micrometer-level motions. This defect is problematic because the amplitude of these variations is central to the method.

Another type of dendrometer, a strain-gauge dendrometer, is available but much less common. Strain-gauge dendrometers still encounter friction in the underlying mechanism. Additionally, the form factor of a strain gauge makes it challenging to scale the design down for smaller applications; they are best suited for tracking fruit diameter or other dimensions of larger magnitudes. Furthermore, the accuracy of the strain gauge dendrometer is 50 microns over 20° C., which is an order of magnitude less than other designs. All currently available dendrometers use materials that are temperature sensitive. As outdoor air temperature changes, the dendrometer materials and/or components will experience expansion or contraction as well, often impossible to distinguish from the true changes in the stem dimensions.

Current methods and apparatus for detection of plant water stress include soil water content or other soil-based measurements, pressure chamber to measure leaf or stem water potential, sap flow measurements using sensors embedded in the trunks of trees or vines, and band and point dendrometers. Soil-based sensors often imprecisely represent plant water availability. Pressure chamber requires a significant input of labor to properly monitor plant water status and widespread integration of the required equipment. Further, pressure chamber cannot realistically provide continuous, real-time measurements. Sap flow measurements are unable to pinpoint water stress as the source. Further, probes used for sap flow measurements wound the plant as the probe is inserted and may also negatively affect probe response over time.

BRIEF DESCRIPTION OF THE DRAWINGS

The embodiments of the disclosure will be understood more fully from the detailed description given below and from the accompanying drawings of various embodiments of the disclosure, which, however, should not be taken to limit the disclosure to the specific embodiments, but are for explanation and understanding only.

DETAILED DESCRIPTION

Figure 1:
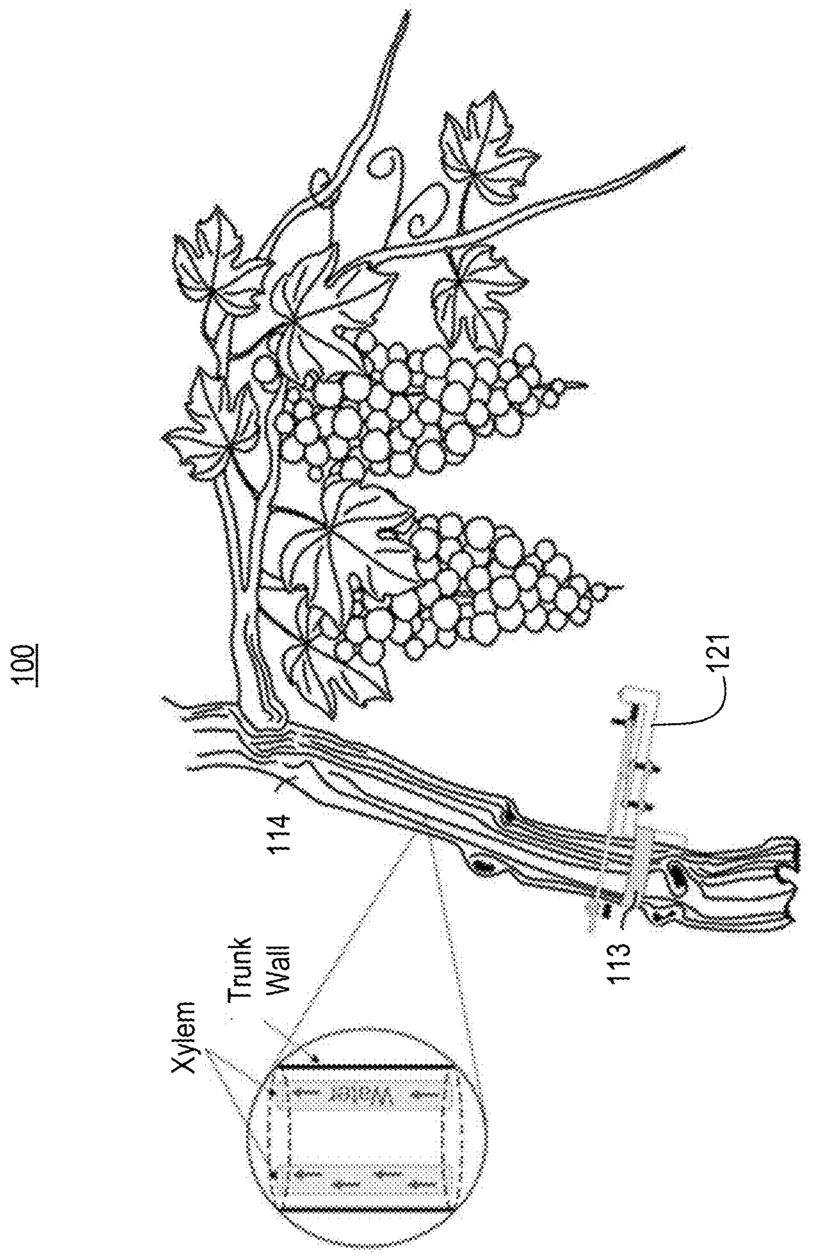
FIG. 1 illustrates a dendrometer on a grapevine trunk and the plant physiology that induces diurnal fluctuations in trunk diameter, in accordance with some embodiments.

Various embodiments describe a magnetic dendrometer configured in a mechanical device. In some embodiments, the magnetic dendrometer comprises a frame and spring-tension mechanism. In some embodiments, the magnetic dendrometer comprises a magnet for moving together with the spring-tension mechanism. In various embodiments, the magnetic dendrometer comprises a magnetic sensor. The magnetic sensor senses the linear motion of the magnet. This linear motion translates to trackable fluctuations in magnetic field. The magnetic fluctuations are converted to electrical signals by the magnetic sensor, in accordance with various embodiments. In some embodiments, the magnetic dendrometer comprises a spring attached to a free-floating wishbone-style component. In various embodiments, the free-floating wishbone-style component is couped to slider which has an adjustable, single-contact point with a target (e.g., a vine, a branch, etc.). In some embodiments, the magnetic dendrometer comprises a stationary frame for carrying the magnetic sensor, connected via the spring to the wishbone/slider combination (the moving components), configured to cooperate with each other for providing linear motion to extend or contract the spring in length directions. The length variations of the dendrometer spring are configured to be converted to linear motion of the magnet and then into electronic signals by the electronic component, in accordance with various embodiments.

In some embodiments, the magnetic sensor is part of an ensemble of electronic components that are used to collect data associated with linear motion of the magnet, and also to process the data. In some embodiments, the electronic components include an encoder. In some embodiments, the encoder is a high-resolution magnetic encoder or sensor. In some embodiments, the free-floating wishbone-style component, slider, and other stationary, but mechanical, components of the magnetic dendrometer are fabricated with carbon fiber or any other suitable material with substantially zero or very low temperature function. For example, the material may not fluctuate (e.g., expand or contract) between extreme temperatures (e.g., below freezing (e.g., below 32° F.) or extreme hot exterior (e.g., over 120° F.) temperatures). The free-floating wishbone-style component and slider are part of the mechanical body. In some embodiments, the dendrometer comprises a spring for connecting opposing contact points of the dendrometer on the body it's installed on. In some embodiments, the dendrometer mechanical body, the electronic component, and/or the magnetic encoder are weatherproof, scratchproof, dustproof, and/or shockproof. In some embodiments, the mechanical body, the electronic component, and/or the magnetic encoder are protected against intrusion of solid particles, liquid, mechanical impact, electric shock, or a combination of these.

In some embodiments, the magnetic dendrometer is coupled to a data logger that is connected to the magnetic encoder for readying the magnetic and electronic signals. In some embodiments, the magnetic dendrometer is coupled to a cable, wherein the cable is used for connecting the magnetic encoder to the remaining electronic component and data logger. In some embodiments, the data logger comprises an electrical energy source for powering the data logger. In some embodiments, the data logger comprises a memory device for data storage. In some embodiments, the data logger further comprises an antenna for signal transmission and reception. In some embodiments, the magnetic dendrometer comprises a temperature and humidity sensor for comparing displacement trends to ambient conditions.

In some embodiments, a sensor network is provided which comprises a network of dendrometers. In some embodiments, the network of dendrometers includes a collection of dendrometers coupled in a network connected via (wired or wireless) communication to a gateway node that collects and aggregates dendrometer data for presentation to a user or database. In some embodiments, the sensor network comprises at least one radio transceiver having an aerial for providing communication between the dendrometer, the gateway node or other computing devices.

There are many technical effects of various embodiments. For example, the dendrometer of various embodiments provides a zero-friction or substantially zero-friction apparatus using linear magnetic encoder and spring mechanism that eliminates or substantially eliminates all friction points from the dendrometer. The carbon fiber fabricated mechanical body allows for near-zero thermal expansion coefficient. The dendrometer of various embodiments includes telemetry ability for real-time tracking of dendrometer data. In some embodiments, a light emitting diode (LED) is provided with or for the dendrometer that allows for quickly evaluating system status from the field (where the dendrometer is used). The magnetic encoder of various embodiments does not have a temperature sensitivity like LVDTs. In various embodiments, the free-floating wishbone-style component has grooves that are used for quickly adjusting the location of the slider. The free-floating wishbone-style component enables tension in the spring to be accomplished on various target objects (e.g., stems, vines, trunks or various sizes). In some embodiments, the position of the magnetic encoder can be adjusted by moving it along a frame by loosening nuts on a sensor plate and sliding the sensor plate. In some embodiments, the magnetic encoder is clamped onto the frame using compression or adhesive (e.g., epoxy). In some embodiments, the magnet is held onto the frame using compression or adhesive. The dendrometer of various embodiments can be hooked into a network of dendrometers to monitor health of large number of objects (e.g., stems, vines, trunks or various sizes) in one or more fields. The data collected from the dendrometer can be processed in a central computer, server, or the cloud, and where the data or results are accessible by a mobile application or software. The results processed from the dendrometers can be used to prove irrigation scheduling information. For instance, the results can indicate when plants need to be watered and how much water each specific plot or field needs. The mobile application can also provide plant-specific care guidance. Other technical effects will be evident from the various embodiments and figures.

The embodiments of the disclosure will be understood more fully from the detailed description given below and from the accompanying drawings of various embodiments of the disclosure, which, however, should not be taken to limit the disclosure to the specific embodiments, but are for explanation and understanding only.

In the following description, numerous details are discussed to provide a more thorough explanation of embodiments of the present disclosure. It will be apparent, however, to one skilled in the art, that embodiments of the present disclosure may be practiced without these specific details. In other instances, well-known structures and devices are shown in block diagram form, rather than in detail, to avoid obscuring embodiments of the present disclosure.

Note that in the corresponding drawings of the embodiments, signals are represented with lines. Some lines may be thicker, to indicate more constituent signal paths, and/or have arrows at one or more ends, to indicate primary information flow direction. Such indications are not intended to be limiting. Rather, the lines are used in connection with one or more exemplary embodiments to facilitate easier understanding of a circuit or a logical unit. Any represented signal, as dictated by design needs or preferences, may actually comprise one or more signals that may travel in either direction, and may be implemented with any suitable type of signal scheme.

It is pointed out that those elements of the figures having the same reference numbers (or names) as the elements of any other figure can operate or function in any manner like that described but are not limited to such.

FIG. 1 illustrates working case 100 having a dendrometer on a grapevine trunk and the plant physiology that induces diurnal fluctuations in trunk diameter, in accordance with some embodiments. The example working case 100 illustrates a hose clamp 113, branch 114, and dendrometer 121 coupled to the hose clamp 113 which in turn is coupled to branch 114. Branch 114 can be any object whose diameter fluctuates with changing environment. In this example, branch 114 is a stem, vine, or trunk.

The diameter of a plant stem/vine/trunk 114 fluctuates daily in response to the stomatal activity. Stomata are the parts of the plant that allow transpiration to occur; when they are open, water flows through the plant, but transpiration is restricted when they are closed. Water is taken up from the soil by the roots and is carried through the plant via the xylem until it is released into the atmosphere via the stomata. Differences in soil water potential and atmospheric water potential enable this mechanism. The water stress that plants experience (whether it is too much or too little water) is directly related to the opening and closing of stomata. For example, plants have been shown to close their stomata in drought conditions. Water stress is also related to how much water is moving through the plant at a given time. The variation in water flow through the xylem is reflected in micrometer-scale fluctuations in plant stem 114 diameter. In various embodiments, dendrometer 121 is used to sense these fluctuations in the stem diameter.

Figure 2:
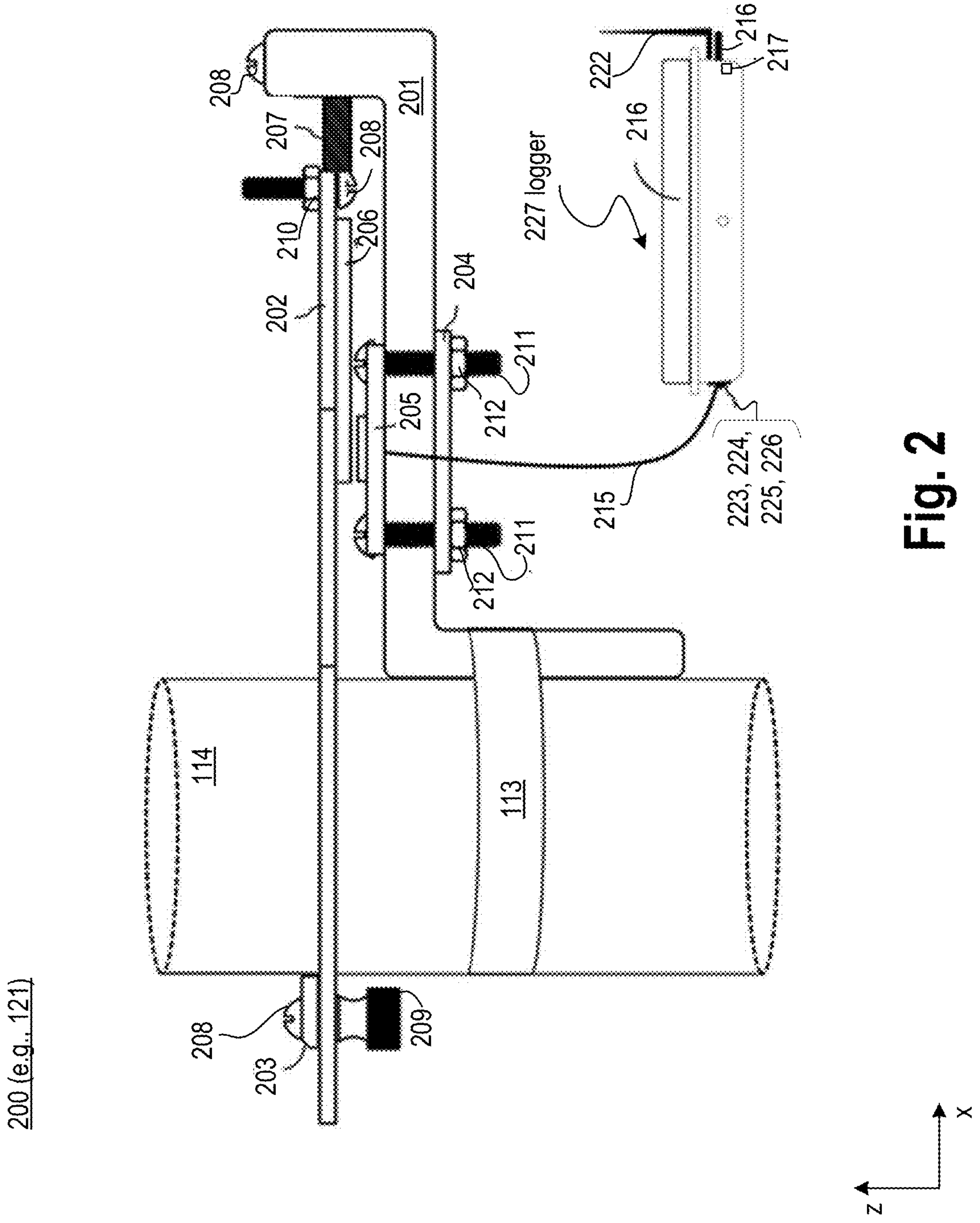
FIG. 2 illustrates a dendrometer that is installed on the trunk of a woody-perennial, in accordance with some embodiments.

FIG. 2 illustrates dendrometer system 200 (e.g., including dendrometer 121) that is installed on the trunk of a woody-perennial, in accordance with some embodiments. In some embodiments, dendrometer 121 comprises a 3-part mechanical system (e.g., carbon-fiber material) of a frame 201, wishbone 202, and slider 203, sensor plate 204, magnetic sensor 205, magnet 206, spring 207, screw fastener 208 (e.g., 2-56 roundhead screw fastener), nut fastener 209 (e.g., 2-56 thumb nut fastener), nut fastener 210 (e.g., 2-56 Hex nut fastener), screw fastener 211 (e.g., 3-48 roundhead screw fastener), nut fastener 212 (e.g., 3-48 Hex nut fastener), and hose clamp 113. In various embodiments, dendrometer system 200, which includes dendrometer 121, also includes cable 215, waterproof case 216, temperature or humidity sensor 217, node antenna 222, LED system 223, button 224, LED plug 225, cable gland 226, and data logger 227.

In various embodiments, the 3-part carbon-fiber mechanical system of frame 201, wishbone 202, and slider 203 creates a frictionless spring-tension mechanism for tracking the diurnal fluctuation in stem diameter. In some embodiments, frame 201 is held tightly against the vine or stem with a hose clamp 113. In various embodiments, frame 201 is a main attachment point between vine 114 and dendrometer 121, and holds spring 207 in place. In some embodiments, spring 207 has a tension of 0.91 lbs/in. In other embodiments, other types of springs may be used to adjust or calibrate sensitivity of linear displacement. In some embodiments, wishbone 202 is a mount for magnet 206 and slider 203. In various embodiments, wishbone 202 provides connection between spring 207 and target object (e.g., vine) motion. In some embodiments, slider 203 holds dendrometer 121 (also referred to as a device) in tension and is used against the far side of the target object 114. In some embodiments, slider 203 is removable and its placement is adjustable. In some embodiments, slider 203 is configured to be used for installing the device and moving magnet 206 and spring 207 in response to target object diameter fluctuations. In various embodiments, hose clamp 113 secures frame 201 against the target object (e.g., plant).

In various embodiments, magnetic sensor 205 tracks linear motion of magnet 206 using the changes in a magnetic field. In some embodiments, magnetic sensor 205 is an encoder that encodes the linear motion of magnet 206 into a fine resolution (e.g., micrometer resolution). An example of magnetic sensor 205 is an AS5311 linear sensor with 0.5 micrometer resolution by the AMS OSRAM group. Other than magnetic sensor 205 may also be used. In various examples, resolution of magnetic sensor 205 is expected to be high enough to achieve a precision of 10 μm/m or better.

In some embodiments, magnet 206 moves together with wishbone 202 and its displacement is tracked. In some embodiments, magnetic sensor 205 is connected via cable 215 to data logger 227. In some embodiments, magnetic sensor 205 is mounted to frame 201 via a plate 204 and four brass screws 211 (e.g., 3-48 screws). In some embodiments, magnet 206 is above the raised block on magnetic sensor 205 when installed. In various embodiments, magnet 206 is parallel to magnetic sensor 205 for accurate tracking. In various embodiments, plate 204 is fabricated using carbon fiber. In some embodiments, other components (e.g., wishbone 202, slider 203, and plate 204) are fabricated using carbon fiber. Carbon fiber has extremely low coefficient of thermal expansion and light weight. Expansion and contraction of the device materials can skew data and limit reliability and accuracy. When the material expands, the instrument measures fluctuations in both the tool and the plant as opposed to only the plant stem. Given the small magnitude of diurnal fluctuations in vines (typically 100 μm-150 μm), minimizing temperature sensitivity is useful for accurate crop evaluation and providing useful guidance on crop care. The carbon fiber construction of various components of dendrometer 121 reduces temperature sensitivity. In some embodiments, other materials with low or zero temperature sensitivity can be used instead of carbon fiber.

By relying on a spring-loaded design using spring 207, movement recorded by magnetic sensor 205 is guided by tension, in accordance with various embodiments. For example, there is no mechanical contact between parts in opposition that generally impedes upon measurement accuracy. Dendrometer 121 allows spring 207 to move freely. For instance, there is no rubbing (or substantially no rubbing) on any device surface and magnet 206 floats above sensor 205. By using a frictionless mechanism, mechanical hysteresis is eliminated, facilitating accurate quantification of fluctuations in diameter of the target object, in accordance with various embodiments.

In some embodiments, antenna 222 may comprise one or more directional or omnidirectional antennas, including monopole antennas, dipole antennas, loop antennas, patch antennas, microstrip antennas, coplanar wave antennas, or other types of antennas suitable for transmission of Radio Frequency (RF) signals. In some multiple-input multiple-output (MIMO) embodiments, Antenna(s) 222 are separated to take advantage of spatial diversity.

In some embodiments, dendrometer 200 includes LED Indication System indicated by references signs 223, 224, 225 that can verify proper relative vertical positioning between the magnet 206 and the sensor 205. In some embodiments, other electronics are enclosed in a waterproof case 216 (e.g., a Pelican Case). In some embodiments, cable glands 226 allow passage between the inside and outside of the enclosure. In some embodiments, LED 223 and button 224 used in the LED indication system are attached to case 216. In some embodiments, waterproof case 216 can be attached to the wire trellis running through the rows of the vineyard (or other crop environment) via a carabiner.

Figure 3:
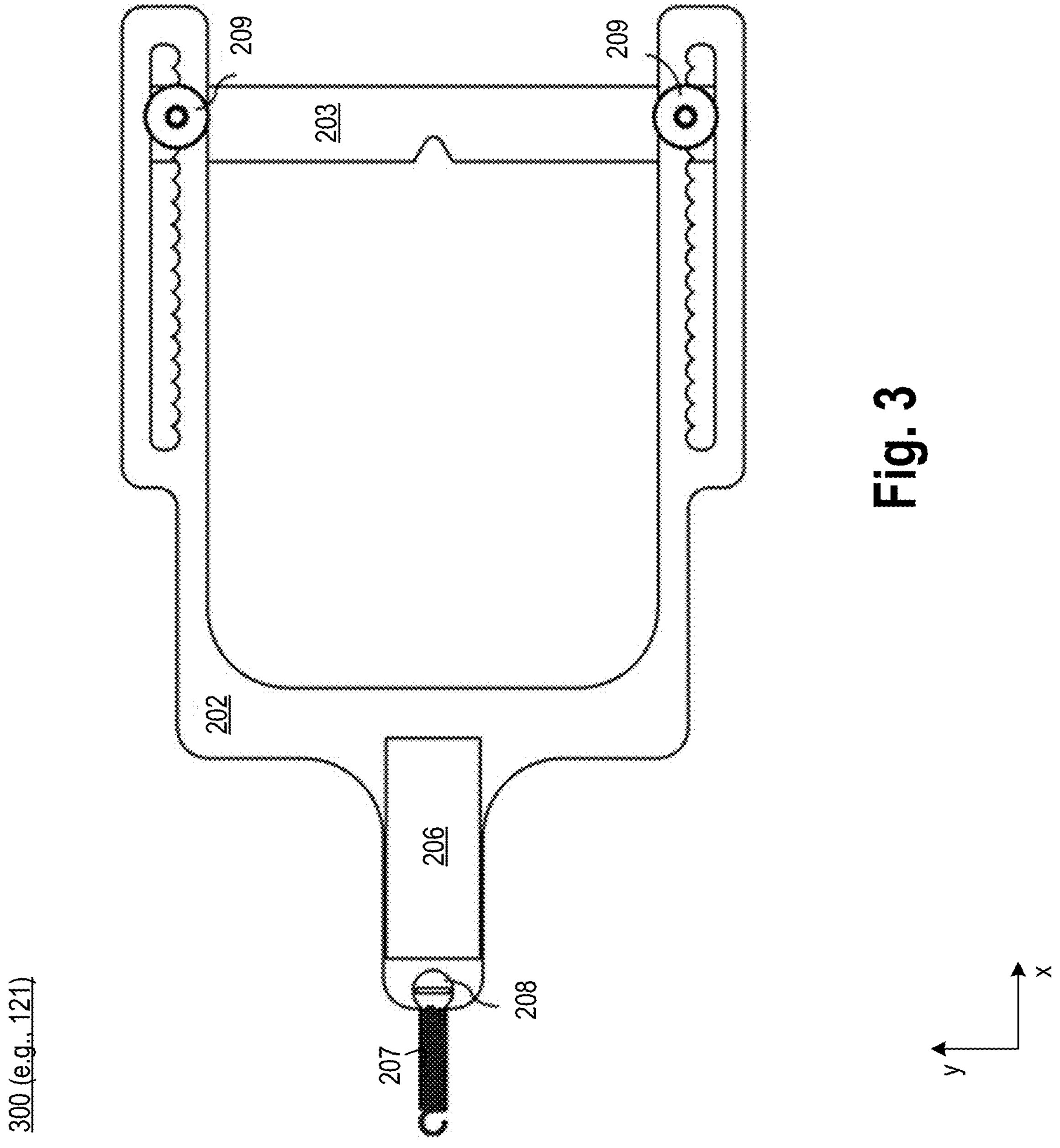
FIG. 3 illustrates primary moving mechanical components of the dendrometer with fasteners and sensing magnet, wishbone, slider, and spring, in accordance with some embodiments.

FIG. 3 illustrates top view 300 of the primary moving mechanical components of dendrometer 121 with fasteners (e.g., 208, 209, 210) and sensing magnet 206, wishbone 202, slider 203, and spring 207, in accordance with some embodiments. In some embodiments, wishbone 202 is a two-prong structure (e.g., 100 mm long and 62 mm wide). In other embodiments, other shapes for wishbone 202 can be used based on the shape of the target object. The dimensions can be scaled to accommodate various applications of dendrometer 121. In some embodiments, magnet 206 is epoxied to the stem (or arm) of wishbone 202. Any suitable adhesive (e.g., epoxy) may be used for connecting magnet 206 to the stem of wishbone 202. In some embodiments, sensor 205 is attached to a sensor plate via compression. In some embodiments, sensor 205 is attached to the sensor plate via epoxy. Any suitable means can be used for attaching sensor 205.

In some embodiments, one end of spring 207 hooks onto screw 208 (e.g., a 2-56 screw) on the end of the wishbone 202 and is clamped down by nut 210. When installing the device on a target object (e.g., plant), the position of slider 203 can be adjusted by loosening thumb nuts 209 and gently squeezing together the arms of the wishbone 202. In some embodiments, slider 203 can be moved to a different set of grooves; when the arms are released, it locks into place and thumb nuts 209 can be tightened to ensure stability. In some embodiments, slider 203 can be completely removed from wishbone 202 so that dendrometer 121 can be placed around a target object (e.g., tree, vine, stem, etc.). The cutout in slider 203 indicates its center point. This cutout can be used for reference when aligning slider 203 during installation, in accordance with some embodiments.

Figure 4A:
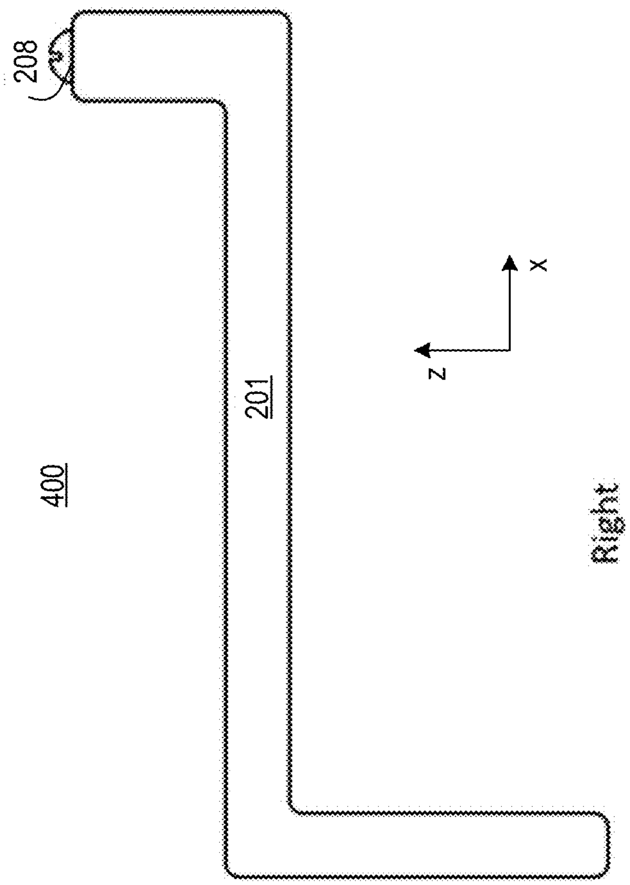
FIGS. 4A-B illustrate side views and, right view and front view, respectively, of frame, in accordance with some embodiments.
Figure 4B:
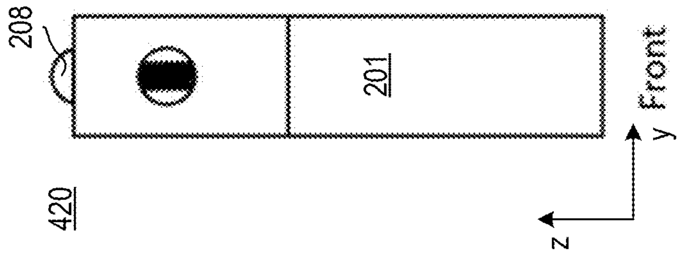

FIGS. 4A-B illustrate side views 400 and 420, right view and front view, respectively, of frame 201, in accordance with some embodiments. In one example, frame 201 is 68 mm long along the x-axis and 9.5 mm wide along the z axis. Screw 208 (e.g., brass 2-56 screw) inside frame 201 holds the other end of spring 207. In some embodiments, a hole (e.g., a 4.5 mm hole) on the front face of frame 201, located below the face of the frame 201 (e.g., 7.4 mm below the face of frame 201) that the screw head rests on, allows the spring 207 to hook onto screw 208 without touching frame 201. In some embodiments, magnetic sensor 205 is held against frame 201 via sensor plate 204; both remain stationary once dendrometer 121 is assembled and deployed.

Figure 5:
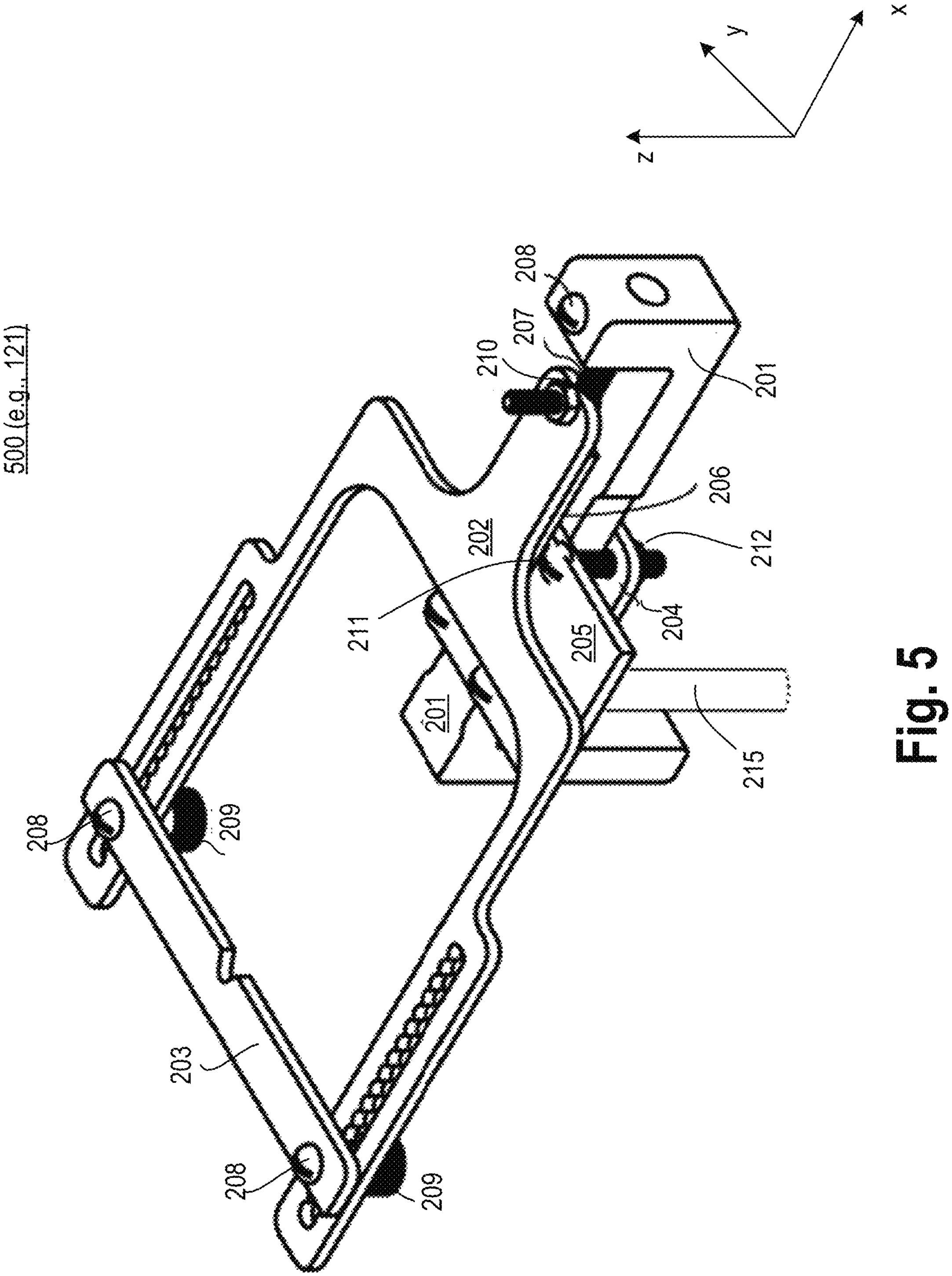
FIG. 5 illustrates a mechanical body of the dendrometer, in accordance with some embodiments.

FIG. 5 illustrates mechanical body 500 of dendrometer 121, in accordance with some embodiments. FIG. 5 illustrates an isometric view of the assembled mechanical components of the dendrometer 121 with magnetic sensor 205 with cable 215 (e.g., CAT5 cable) attached. In some embodiments, a waterjet cutter can be used to manufacture wishbone 202, slider 203, and frame 201.

Figure 6:
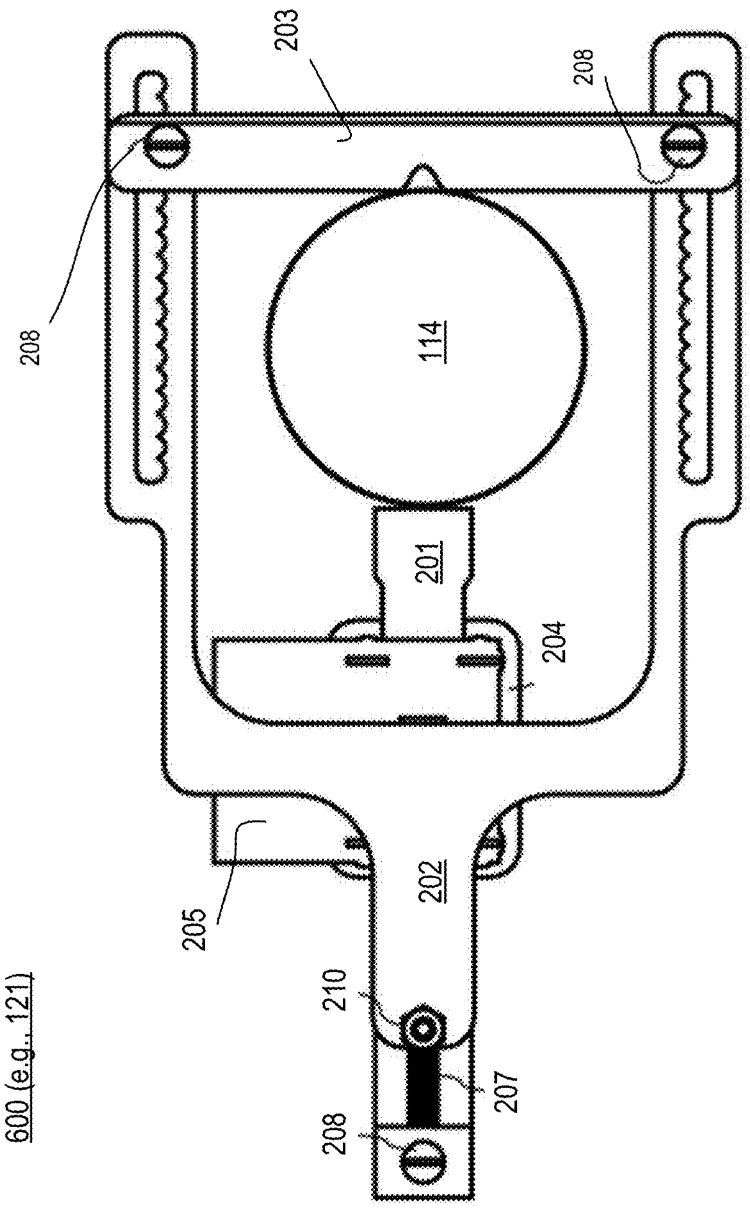
FIG. 6 illustrates a top view of an assembled dendrometer on a plant trunk, in accordance with some embodiments.

FIG. 6 illustrates top view 600 of an assembled dendrometer 121 on plant trunk 114, in accordance with some embodiments. In various embodiments, when stem 114 diameter expands, slider 203 is pushed outward and spring 207 is stretched. Since slider 203 is secured onto wishbone 202 (note, its relative position along wishbone may be fixed in place upon installation), which is connected to spring 207, magnet 206 that is on wishbone 202 experiences the same horizontal movement as slider 203. In some embodiments, magnetic sensor 205 can track the linear movement of magnet 206 through the change in magnetic field strength. In some embodiments, screws 211 (e.g., 3-48 screws) used to clamp magnetic sensor 205 and mount 204 (or sensor plate that holds magnetic sensor 205 against frame 201) are filed on top to stop them from impeding on the motion of magnet 206. Before installation, the bark on the trunk is trimmed or rubbed away, providing two parallel strips of relatively smooth surface (living tissue of the trunk is not affected by the removal). The arms of the wishbone 202 may not touch the body dendrometer 121 is installed on. Note, that spring 207 may be engaged in a light-to-moderate amount (e.g., extending about 1-5 mm past equilibrium/rest position) when installed to create tension.

Figure 7:
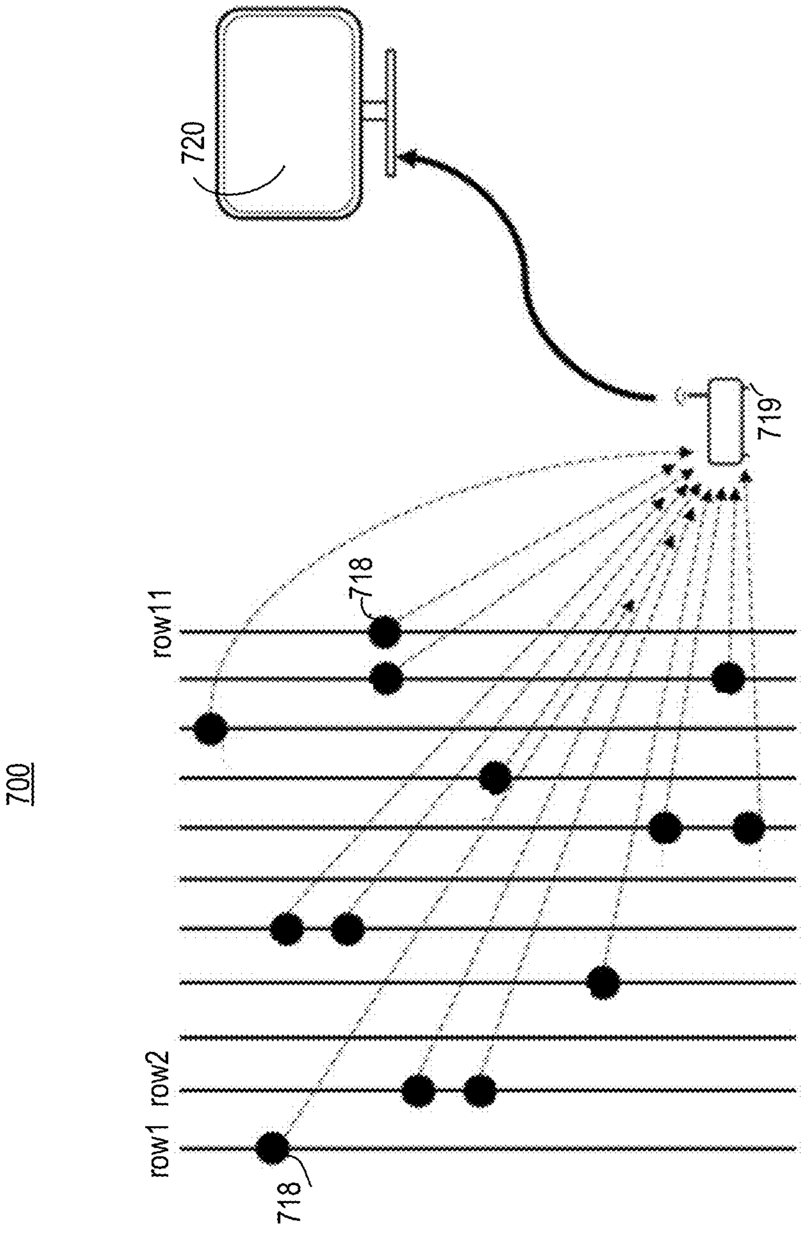
FIG. 7 illustrates a sensor network that the dendrometer uses to transfer data, in accordance with some embodiments.

FIG. 7 illustrates sensor network 700 that the dendrometer uses to transfer data, in accordance with some embodiments. Sensor network 700 illustrates a plurality of dendrometer nodes 718 (e.g., system 200) attached to a sample of trunks per row in a field. In this example, 11 rows of plants are shown. Any number of dendrometer nodes 718 may be used and its data analyzed. In some embodiments, dendrometer nodes 718 are wirelessly connected to a central hub 719 through telemetry (indicated by dotted lines) that transfers data. The central hub 719 can be a cloud, server, computer, etc. In some embodiments, processed data from central hub 719 is displayed or reported on display 720.

Display 720 represents hardware (e.g., display devices) and software (e.g., drivers) components that provide a visual and/or tactile display for a user to interact with controller hub 719. Display 720 includes a display interface which includes the particular screen or hardware device used to provide a display to a user. In one embodiment, the display interface includes logic to perform at least some processing related to the display. In one embodiment, display 720 includes a touch screen (or touch pad) device that provides both output and input to a user. In various embodiments, the data from dendrometer nodes 718 is collected in real-time and processed as data arrives, and is then displayed on display 720. In some embodiments, a mobile application can be used to access data from central hub 719. In some embodiments, function of central hub 719 is implemented by mobile phone or a mobile processing device.

Figure 8:
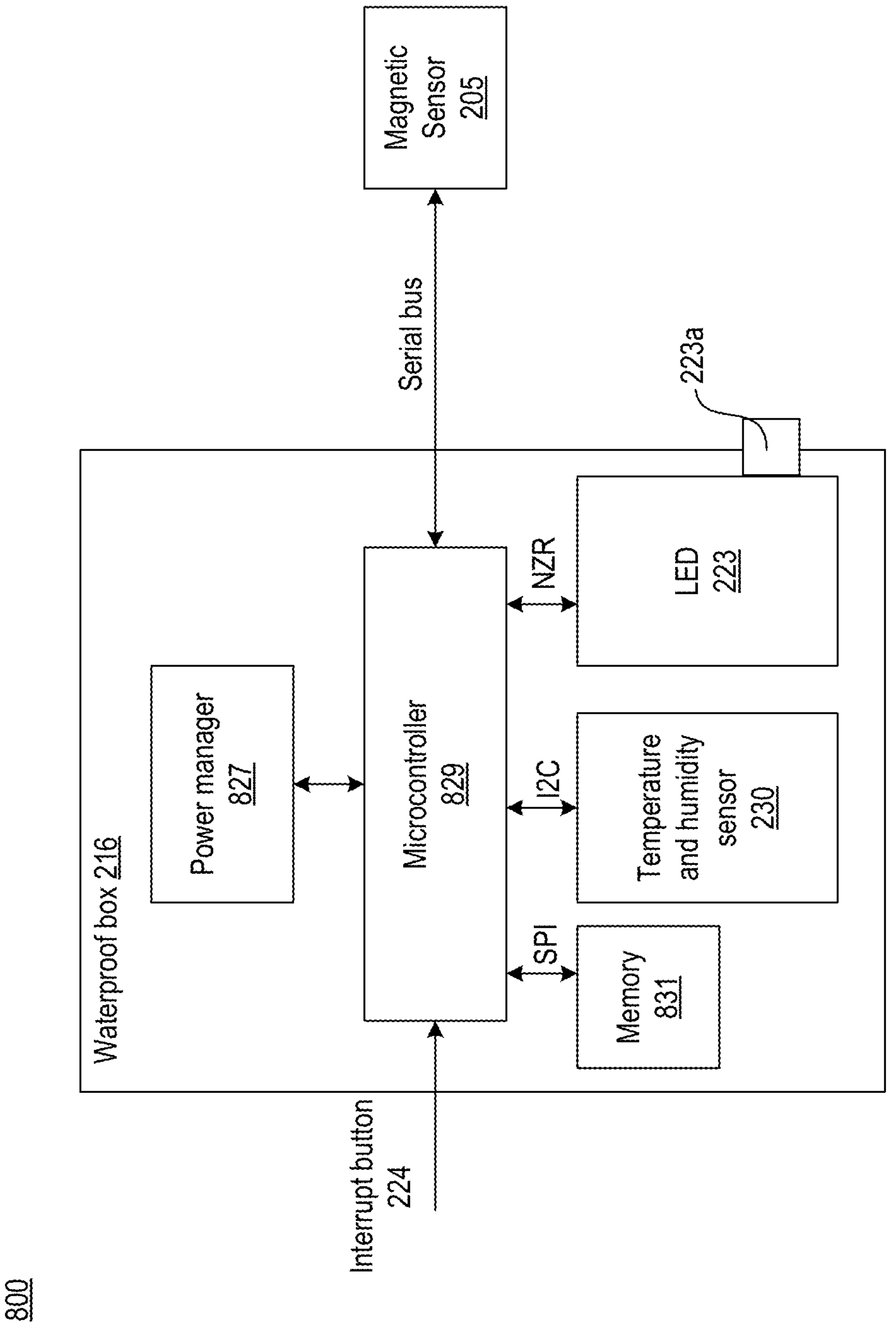
FIG. 8 illustrates a schematic of a data logger for a magnetic sensor and light emitting diode (LED) indication system, in accordance with some embodiments.

FIG. 8 illustrates computer system 800 with a schematic of a data logger for a magnetic sensor and light emitting diode (LED) indication system, in accordance with some embodiments. In some embodiments, computer system 800 includes one or more processors in waterproof box 216 which is communicatively coupled to magnetic sensor 205. In some embodiments, the one or more processors in waterproof box 216 include power manager 827, microcontroller 829, memory 831, temperature and humidity sensor 217 and LED system 223. These various components in waterproof box 216 may include other components including an audio subsystem, a display subsystem, an I/O controller, connectivity, and peripheral connections.

In some embodiments, power manager 827 manages battery power usage, charging of the battery, and features related to power saving operation. In some embodiments, power manager 827 controls the power consumption of microcontroller 829 and other components. For example, power manager 827 can clock gate, power gate, or apply any other power management techniques. In some embodiments, power manager 827 is operable to data log and time keep the various sensors coupled to dendrometer 121. In some embodiments, magnetic sensor 205, LED 223, button 224, and temperature and humidity sensor 217 are powered through power manager 827, which acts as a relay that turns the power on and off to the sensors to conserve battery. While not shown, in some embodiments, a printed circuit board is provided that breaks out the connections to standard JST wire ports that can be connected to the sensors.

In some embodiments, microcontroller 829 can include one or more physical devices, such as microprocessors, graphics processor, accelerator, inference logic, computational processor, application processors, microcontrollers, programmable logic devices, or other processing means. The processing operations performed by microcontroller 829 include the execution of an operating platform or operating system on which applications and/or device functions are executed. The processing operations include operations related to I/O (input/output) with a human user or with other devices, operations related to power management, and/or operations related to connecting waterproof box 216 to another device (e.g., control hub 719, magnetic sensor 205). The processing operations may also include operations related to audio I/O and/or display I/O. In some embodiments, microcontroller 829 executes the scheme of analyzing or processing electrical signals from magnetic sensor 205. In some embodiments, magnetic sensor 205 is coupled to microcontroller 829 via a serial bus. In some embodiments, microcontroller 829 can be reset, powered on, or interrupted using interrupt button 224. In some embodiments, microcontroller 829 communicates with memory 831 using a serial peripheral interface (SPI). In some embodiments, microcontroller 829 communicates with memory 831 using an I2C interface. In some embodiments, microcontroller 829 communicates with memory 831 using non-return-to-zero (NRZ) signal interface.

In some embodiments, memory 831 includes memory devices for storing information. Memory 831 can include nonvolatile (state does not change if power to the memory device is interrupted) and/or volatile (state is indeterminate if power to the memory device is interrupted) memory devices. Examples of nonvolatile memory include flash memory, magnetic memory, resistive memory. Examples of volatile memory include static random-access memory, dynamic random-access memory, etc. Memory 831 can store application data, user data, documents, or other data, as well as system data (whether long-term or temporary) related to the execution of the applications and functions of the computing system.

Elements of embodiments are also provided as a machine-readable medium (e.g., memory 831) for storing the computer-executable instructions (e.g., instructions to implement any other processes discussed herein). The machine-readable medium (e.g., memory 831) may include, but is not limited to, flash memory, optical disks, CD-ROMs, DVD ROMs, RAMs, EPROMs, EEPROMs, magnetic or optical cards, phase change memory (PCM), or other types of machine-readable media suitable for storing electronic or computer-executable instructions. For example, embodiments of the disclosure may be downloaded as a computer program (e.g., BIOS) which may be transferred from a remote computer (e.g., a server) to a requesting computer (e.g., a client) by way of data signals via a communication link (e.g., a modem or network connection).

In some embodiments, audio subsystem represents hardware (e.g., audio hardware and audio circuits) and software (e.g., drivers, codecs) components associated with providing audio functions to the computing system. Devices for such functions can be integrated into the computing system or connected to the computing system. Audio functions can include speaker and/or headphone output, as well as microphone input. In some embodiments, a user interacts with the computing system by providing audio commands that are received and processed by microcontroller 829.

In some embodiments, the computing system including connectivity can include multiple different types of connectivity. The computing system may include cellular connectivity and wireless connectivity. Cellular connectivity refers generally to cellular network connectivity provided by wireless carriers, such as provided via GSM (global system for mobile communications) or variations or derivatives, CDMA (code division multiple access) or variations or derivatives, TDM (time division multiplexing) or variations or derivatives, or other cellular service standards. Wireless connectivity (or wireless interface) refers to wireless connectivity that is not cellular, and can include personal area networks (such as Bluetooth, Near Field, etc.), local area networks (such as Wi-Fi), and/or wide area networks (such as LTE), or other wireless communication.

In some embodiments, LED indication system 223 is implemented to easily check that dendrometer 121 is actively collecting data. In some embodiments, LED indication system 223 comprises a button 224, LED 223*a*, and LED plug 225. When button 224 is pushed, microcontroller 829 or any other suitable logic may check the distance between magnet 206 and magnetic encoder 205 to see if it is still within a required range (e.g., a range of 0.2 mm to 0.4 mm) as well as if magnet 206 is parallel with sensor 205. If it is, LED 223*a* will turn green for a few seconds; this indicates that dendrometer 121 is still accurately recording data. If LED 223*a* turns red, something may have caused the magnet 206 to shift relative to sensor 205, in which case the data may no longer be valid during the previous testing period (when looking at the data, you will likely be able to see a jump when the misalignment event occurred). If this happens, LED indication system 223 may be used to adjust slider 203 until LED 223*a* is green. In some cases, LED 223*a* may appear yellow; this means that the alignment is still in range but is on the very edge. This could impact the precision of the measurements. In this case it may be recommended that the same procedures for adjustment be followed as when LED 223*a* is red. However, if yellow, the data trends can be expected to still be valid. While LED functions are explained with reference to a single LED with three colors, multiple LEDs with any number of colors may be used to conveying information about dendrometer 121.

In some embodiments, magnetic sensor 205 communicates with microcontroller 829 through a serial communication. The serial communication is bit-banged into a serial value that can be converted into a distance or displacement measurement, in accordance with some embodiments. In some embodiments, if magnet 206 is held parallel to magnetic sensor 205 within a distance (e.g., 0.2 mm to 0.4 mm), magnetic sensor 205 may be able to detect magnet 206 and the distance traveled since the last measurement. In some embodiments, microcontroller 829 turns on when the power source is plugged in. In some embodiments, microcontroller 829 enters autonomous operation once magnet 206 and magnetic sensor 205 are properly aligned. In various embodiments, displacement measurements are based on serial values upon device initialization and/or installation. In some embodiments, data values for time, temperature, humidity, serial value, displacement, and vapor pressure deficit are recorded locally in memory 831 and transmitted wirelessly to controller hub 719 via the antenna 222.

Figure 9:
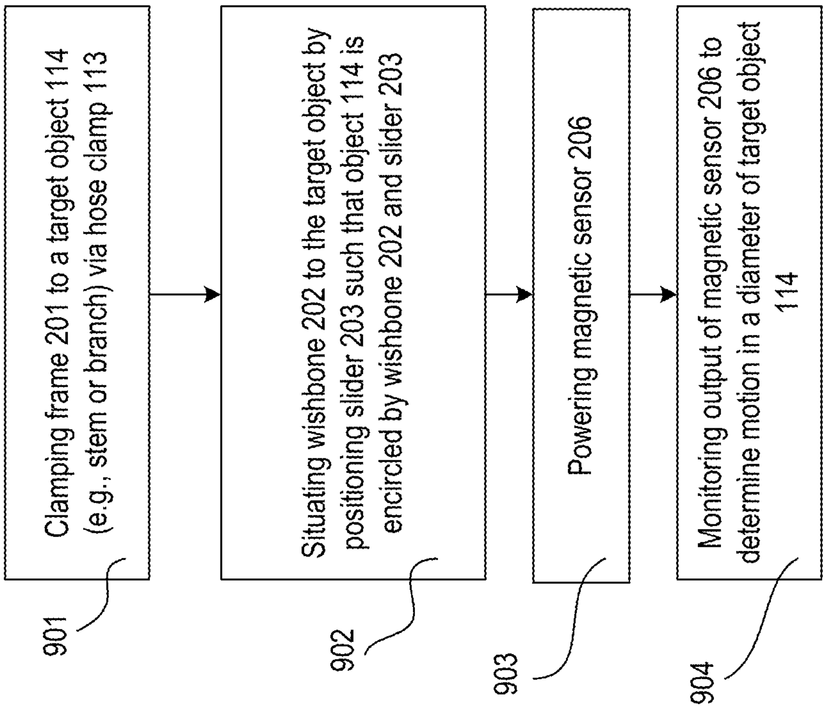
FIG. 9 illustrates a flowchart of a method for operating the dendrometer, in accordance with some embodiments.

FIG. 9 illustrates flowchart 900 of a method for operating the dendrometer, in accordance with some embodiments. While various blocks are illustrated in a certain order, the order can be modified. For example, some blocks may be performed before others while other blocks may be performed simultaneously. Some blocks may be performed by hardware, software, or a combination of them.

At block 901, hose clamp 113 (or a spring clamp) is clamped to target object 114 (e.g., stem or branch). Hose clamp 113 goes around target object 114 and a portion of frame 101, thus holding dendrometer components together. At block 902, wishbone 202 is situated or positioned to partially surround using its sides, legs, or prongs to target object 114, and then secured by situating or positioning slider 203 such that target object 114 is encircled by wishbone 202 and slider 203 together. After slider 203 and wishbone 202 encircles target object 114, the process of detecting fluctuations in the diameter of target object 114 begins. At block 903, magnetic system 205 is powered up. For example, power manager 827 supplies a suitable power supply to magnetic system 205. In some embodiments, an electronic component (e.g., components in waterproof box 216) is connected to dendrometer 121 via cable 215. The electronic component is connected to a data logger for data processing locally, in accordance with some embodiments. At block 904, a display or any computing device is used to monitor the output of magnetic sensor 205. As the diameter changes, data is logged and reported. In some embodiments, the computing device may transmit electronic signals to other device(s) for processing and analyzing data.

In some embodiments, a method is provided for servicing dendrometer 121. The method comprises cleaning magnet 205 and the surface of sensor 206. In some embodiments, the method of servicing dendrometer 121 comprises replacing faulty parts of the mechanical body (e.g., frame 201, wishbone 202, slider 203, spring 207). In some embodiments, the method of servicing dendrometer 121 comprises pushing interrupt button 224, which triggers an evaluation of relative position of magnet 206 with magnetic sensor 205. In some embodiments, LED 223*a* lights up upon pushing interrupt button 224. The color of LED 223*a* indicates whether dendrometer 121 is operating correctly. For example, LED color indicates if the distance between magnet 206 and magnetic sensor 205 is within a range required for operation.

In some embodiments, a method is provided for installing dendrometer 121. The method comprises connecting flexible spring 207 to frame 201 and wishbone 202. In various embodiments, wishbone 202 extends around sides of the target object 114 (e.g., stem, vine, trunk). The two arms of wishbone 202 are connected by slider 203. Wishbone 202 provides a single-contact point on target object 114 for spring-loaded frame 201. In some embodiments, a method is provided for configuring dendrometer 121 by providing a compression-based magnetic encoder sensor mount, examining range of relative movements between magnet 206 and magnetic encoder (or sensor) 205.

Figure 10:
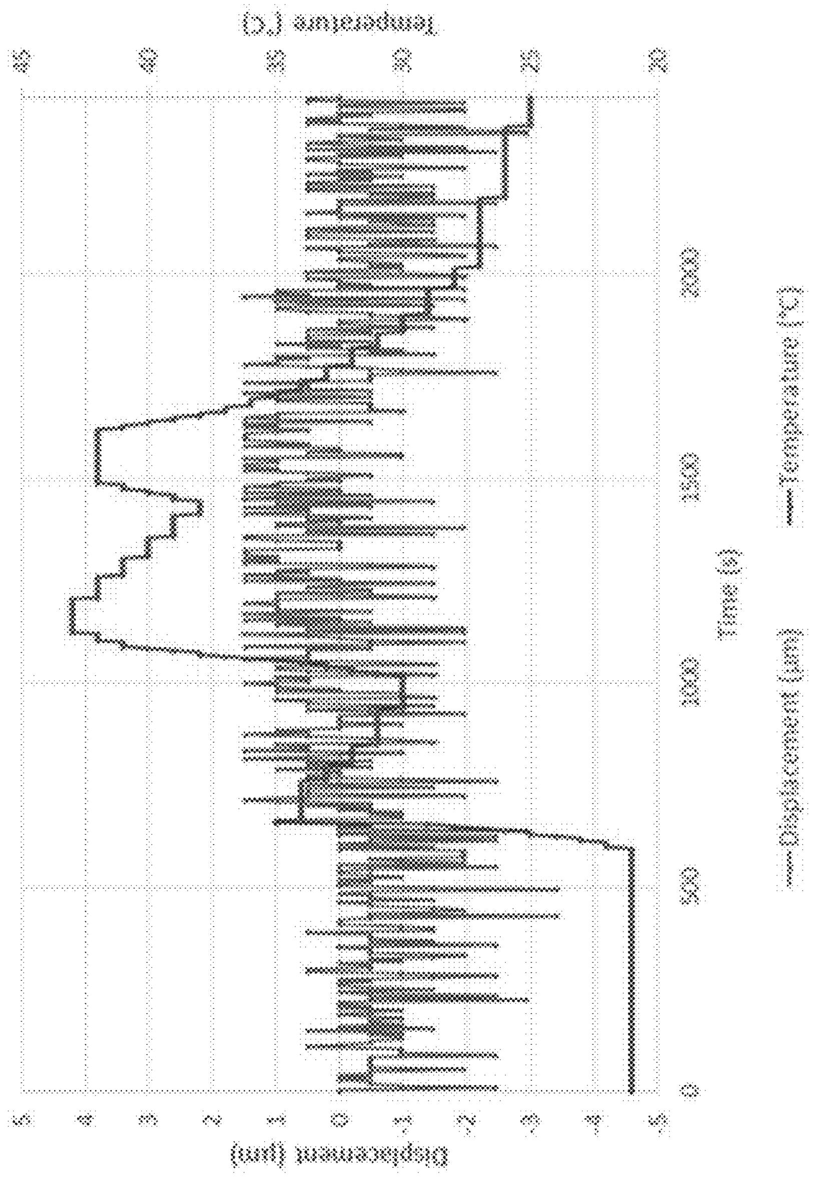
FIG. 10 illustrates a plot showing temperature dependency of the magnetic sensor, in accordance with some embodiments.

FIG. 10 illustrates plot 1000 showing temperature dependency of the magnetic sensor, in accordance with some embodiments. To ensure that linear magnetic sensor readings are not affected by ambient temperature fluctuations, an oven test can be performed with sensor 205. In one example, magnetic sensor 205 and magnet 206 are aligned according to the specifications on magnetic sensor 205, placed in a small oven, and left static throughout the test. The oven is used to create temperature changes. Temperature was measured and data recorded to a memory. In this example, measurements are recorded every five seconds.

Plot 1000 demonstrates that magnetic sensor 205 has an error of 0.002% within a temperature range of 10 degree Celsius to 42 degrees Celsius. As can be seen in plot 1000 with fluctuating temperatures, magnetic sensor 205 is able to output a consistent value; displacement measurements go from a minimum −3.43 μm to a maximum 1.47 μm, creating an overall change of 4.9 μm. The magnitude of the noise in displacement is negligible since daily stem fluctuations are expected to be in the range of 100-200 μm.

Figure 11:
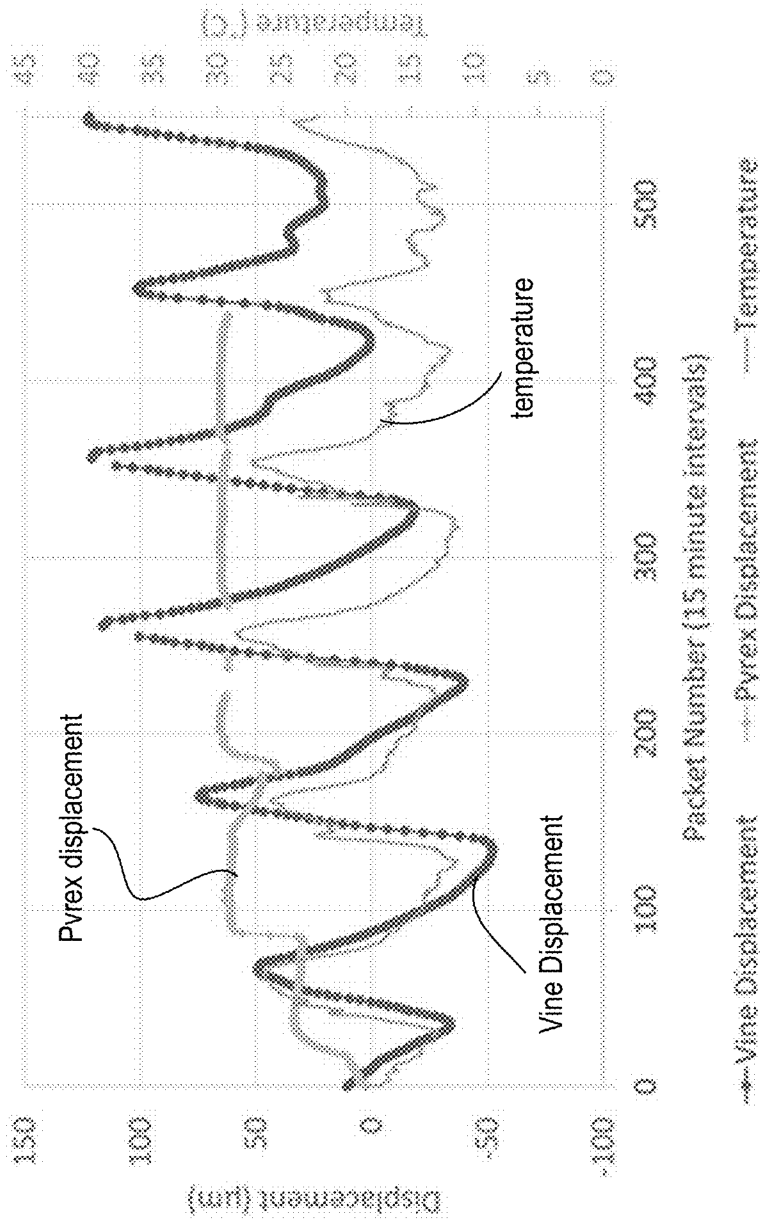
FIG. 11 illustrates a plot showing displacement on a grapevine, displacement on a Pyrex cylinder, and temperature measured by the dendrometer, in accordance with some embodiments.

FIG. 11 illustrates plot 1100 showing displacement on a grapevine, displacement on a Pyrex cylinder, and temperature measured by the dendrometer, in accordance with some embodiments. In this example, one dendrometer is installed on a vine (about ten years old) with a diameter of 26 mm. A second dendrometer is placed on a Pyrex graduated cylinder (known to have an extremely low coefficient of thermal expansion of 4 μm/(m° C.)) to evaluate potential temperature dependency present in the dendrometer system. Plot 1100 shows consistently tracking daily stem diameter changes of approximately 150-200 μm. Plot 1100 also shows that dendrometer 121 is mostly insensitive to temperature fluctuations. In this example, a maximum of 30 μm of movement per day is recorded on Pyrex cylinder.

Figure 12:
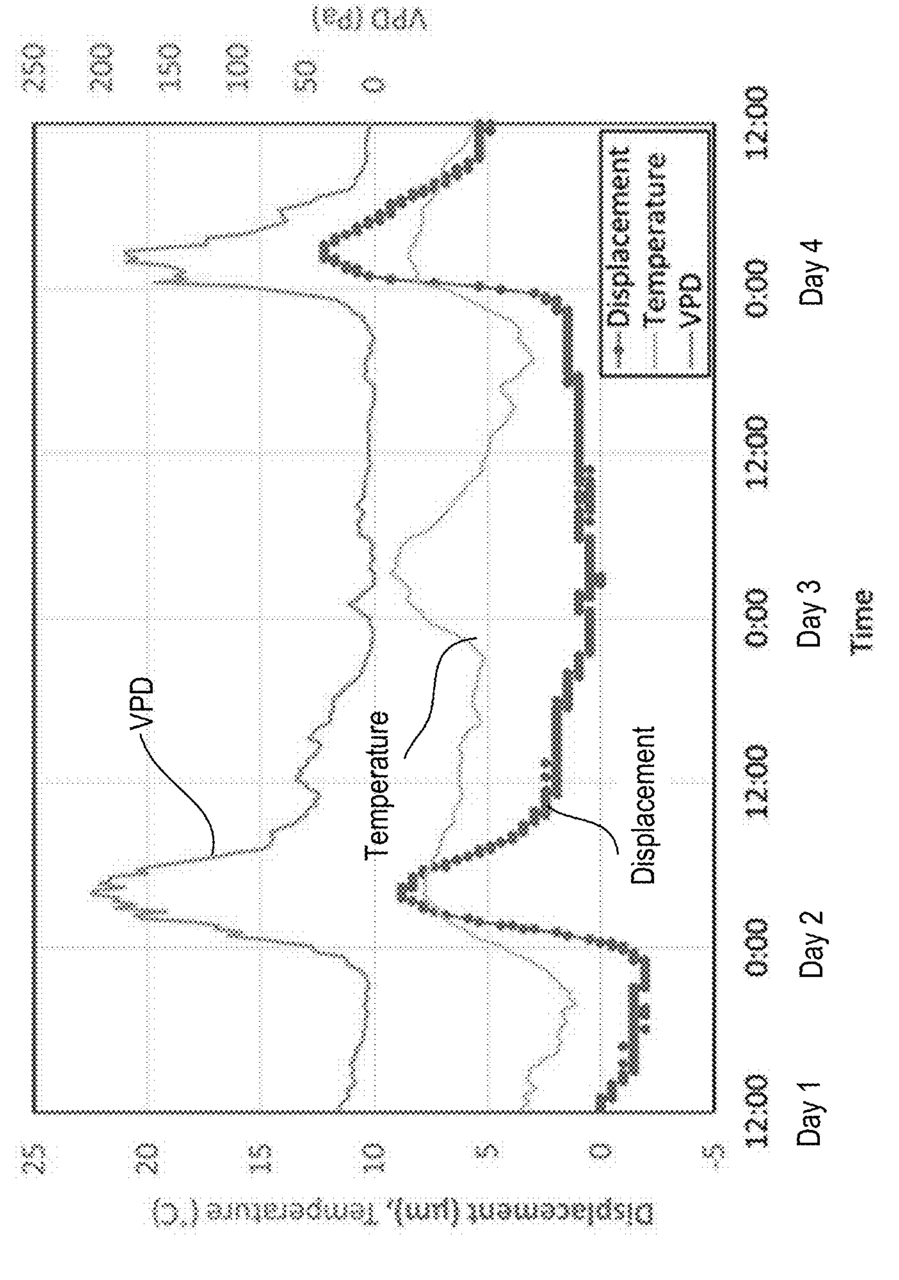
FIG. 12 illustrates a plot showing vine displacement compared with vapor pressure deficit (VPD) and temperature measurements, in accordance with some embodiments.

FIG. 12 illustrates plot 1200 showing vine displacement compared with vapor pressure deficit (VPD) and temperature measurements, in accordance with some embodiments. Vapor Pressure Deficit (VPD) is a function of temperature and relative humidity that measures vapor pressure in the air. VPD is a difference between Saturation Vapor Pressure (SVP), which is the maximum amount of water vapor that air can hold at a given temperature, and Actual Vapor Pressure (AVP), which is the true amount of water vapor in the air. Stem diameter fluctuations are related to leaf and water potentials in plants, which themselves are connected to VPD. There is a strong linear correlation between VPD and leaf and stem water potential in grapevines. Plant stem diameter oscillations follow transpiration and transpiration is driven by VPD; continuous measurements of stem diameter are thereby expected to closely match VPD patterns.

The trends in displacement data from the dendrometer coincide with that of the VPD calculated from the temperature and relative humidity data. On the first full day and third day, the displacement, VPD, and temperature have similar timing for their minimum and maximum values. However, despite a temperature change of 6° C. (maximum of 9° C. and minimum of 3.0° C.) on the second day of testing like the first and third days, the displacement measurements from the dendrometer exhibit almost no change, which is consistent with the VPD trend on that day. Plot 1200 confirms that dendrometer 121 does not have temperature dependence and measurements accurately reflect stem diameter oscillation patterns. Plot 1200 shows dendrometer 121 consistently tracks daily stem diameter between 15-33 μm. Plot 1200 also shows that stem diameter fluctuations show a correlation with VPD and not temperature.

While various embodiments are described with reference to woody perennial plants (e.g., grapevines), dendrometer 121 can be scaled to measure fluctuations and/or growth of stems, branches, or fruit such as apple tree branches and cocoa beans. In another example, dendrometer 121 can be applied to grasses, stalks, bamboo, or other plants. In some embodiments, magnetic sensor 205 can be replaced with LVDT if tolerance for temperature change is accommodated. In some embodiments, dendrometer 121 can have more than one contact point around the circumference of target object 114 for tracking the displacement. For example, the design of dendrometer 121 can be modified by duplicating the mechanical setup so that the diameter is measured along two or more chords (at the same circumference line) for redundancy. This may look like having two or more dendrometers installed at the same height on the plant, but at slightly different points around the circumference.

Dendrometer 121 and its associated components can also be used to evaluate material expansion for things like metal rods in situations where the piece will be exposed to wide ranges of temperatures, in accordance with some embodiments. Dendrometer 121 can be used for research opportunities for viticulturists and horticulturists, including possible extensions into plant communication and large-scale crop dynamics. Dendrometer 121 can be used to track relative location or motion. Dendrometer 121 can be used for monitoring the girth of pipes to predict when they may fail and/or prevent failure from happening. Other uses can also be achieved by dendrometer 121.

Throughout the specification, and in the claims, the term "connected" means a direct connection, such as electrical, mechanical, or magnetic connection between the things that are connected, without any intermediary devices.

The term "coupled" means a direct or indirect connection, such as a direct electrical, mechanical, or magnetic connection between the things that are connected or an indirect connection, through one or more passive or active intermediary devices.

The term "adjacent" here generally refers to a position of a thing being next to (e.g., immediately next to or close to with one or more things between them) or adjoining another thing (e.g., abutting it).

The term "circuit" or "module" may refer to one or more passive and/or active components that are arranged to cooperate with one another to provide a desired function.

The term "signal" may refer to at least one current signal, voltage signal, magnetic signal, or data/clock signal. The meaning of "a," "an," and "the" include plural references. The meaning of "in" includes "in" and "on."

The term "analog signal" refers to any continuous signal for which the time varying feature (variable) of the signal is a representation of some other time varying quantity, i.e., analogous to another time varying signal.

The term "digital signal" refers to a physical signal that is a representation of a sequence of discrete values (a quantified discrete-time signal), for example of an arbitrary bit stream, or of a digitized (sampled and analog-to-digital converted) analog signal.

The term "scaling" generally refers to converting a design (schematic and layout) from one process technology to another process technology and may be subsequently being reduced in layout area. In some cases, scaling also refers to upsizing a design from one process technology to another process technology and may be subsequently increasing layout area. The term "scaling" generally also refers to downsizing or upsizing layout and devices within the same technology node. The term "scaling" may also refer to adjusting (e.g., slowing down or speeding up—i.e. scaling down, or scaling up respectively) of a signal frequency relative to another parameter, for example, power supply level.

The terms "substantially," "close," "approximately," "near," and "about," generally refer to being within +/−10% of a target value.

Unless otherwise specified the use of the ordinal adjectives "first," "second," and "third," etc., to describe a common object, merely indicate that different instances of like objects are being referred to and are not intended to imply that the objects so described must be in a given sequence, either temporally, spatially, in ranking or in any other manner.

For the purposes of the present disclosure, phrases "A and/or B" and "A or B" mean (A), (B), or (A and B). For the purposes of the present disclosure, the phrase "A, B, and/or C" means (A), (B), (C), (A and B), (A and C), (B and C), or (A, B and C).

The terms "left," "right," "front," "back," "top," "bottom," "over," "under," and the like in the description and in the claims, if any, are used for descriptive purposes and not necessarily for describing permanent relative positions.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may," "might," or "could" be included, that particular component, feature, structure, or characteristic is not required to be included. If the specification or claim refers to "a" or "an" element, that does not mean there is only one of the elements. If the specification or claims refer to "an additional" element, that does not preclude there being more than one of the additional elements.

Furthermore, the particular features, structures, functions, or characteristics may be combined in any suitable manner in one or more embodiments. For example, a first embodiment may be combined with a second embodiment anywhere the particular features, structures, functions, or characteristics associated with the two embodiments are not mutually exclusive.

While the disclosure has been described in conjunction with specific embodiments thereof, many alternatives, modifications and variations of such embodiments will be apparent to those of ordinary skill in the art considering the foregoing description. The embodiments of the disclosure are intended to embrace all such alternatives, modifications, and variations as to fall within the broad scope of the appended claims. Where specific details are set forth to describe example embodiments of the disclosure, it should be apparent to one skilled in the art that the disclosure can be practiced without, or with variation of, these specific details. The description is thus to be regarded as illustrative instead of limiting.

The following examples pertain to further embodiments. Specifics in the examples may be used anywhere in one or more embodiments. All optional features of the apparatus described herein may also be implemented with respect to a method or process. The examples can be combined in any suitable manner.

Example 1: A dendrometer comprising: a frame configured to couple to a target object via a clamp; a spring having a first end coupled to the frame; a wishbone coupled to a second end of the spring; an adjustable slider coupled to the wishbone; a magnet on or under the wishbone; and a sensor on or under the frame, wherein the sensor is to detect displacement of the magnet.

Example 2: The dendrometer of example 1 comprises a cable coupled to the sensor.

Example 3: The dendrometer of example 2, wherein the cable is coupled to a computing system.

Example 4: The dendrometer of example 3, wherein the computing system is placed in a waterproof housing.

Example 5: The dendrometer of example 3, wherein the computing system includes a temperature and humidity sensor to compare the displacement with reference to an ambient condition.

Example 6: The dendrometer of example 1, wherein the sensor converts magnetic fluctuations into electrical signals.

Example 7: The dendrometer of example 1, wherein the sensor is attached to the frame via compression or epoxy.

Example 8: The dendrometer of example 1, wherein the adjustable slider includes a notch substantially midway of the adjustable slider.

Example 9: The dendrometer of example 1, wherein the frame and the wishbone comprise carbon fiber.

Example 10: The dendrometer of example 1, wherein the second end of the spring is connected to a screw.

Example 11: The dendrometer of example 1, wherein the sensor has a resolution which is at least 10 μm/m.

Example 12: The dendrometer of example 1, wherein the clamp and the adjustable slider are adjacent to the target object.

Example 13: The dendrometer of example 1, wherein the target object is a trunk of a plant.

Example 14: A system comprising: a plurality of dendrometers, wherein an individual dendrometer is configured to couple to an individual target object from among a plurality of target objects; and a control hub to receive data signals from the plurality of dendrometers, wherein the control hub is to determine fluctuations in the plurality of target objects, wherein the individual dendrometer comprises: a frame configured to couple to the individual target object via a clamp; a spring having a first end coupled to the frame; a wishbone coupled to a second end of the spring; an adjustable slider coupled to the wishbone; a magnet on or under the wishbone; and a sensor on or under the frame, wherein the sensor is to detect displacement of the magnet.

Example 15: The system of example 14, wherein the control hub is coupled to a display.

Example 16: The system of example 14, wherein the control hub is in a cloud.

Example 17: The system of example 14, wherein the adjustable slider includes a notch substantially midway of the adjustable slider.

Example 18: The system of example 14, wherein the frame and the wishbone comprise carbon fiber.

Example 19: An apparatus comprising: a magnetic sensor to track linear motion of a magnet on a wishbone; and a spring-tension mechanism coupled to the wishbone, wherein one end of the spring-tension mechanism is connected to a substantially stationary reference.

Example 20: The apparatus of example 19, wherein the spring-tension mechanism is coupled to a frame, wherein the frame and the wishbone comprise carbon fiber.

An abstract is provided that will allow the reader to ascertain the nature and gist of the technical disclosure. The abstract is submitted with the understanding that it will not be used to limit the scope or meaning of the claims. The following claims are hereby incorporated into the detailed description, with each claim standing on its own as a separate embodiment.

We claim:

1. A system comprising:

a plurality of dendrometers, wherein an individual dendrometer of the plurality of dendrometers is configured to couple to an individual object from among a plurality of objects; and a control hub to receive a first signal from the individual dendrometer, wherein the first signal is indicative of a parameter of the individual object, and wherein the control hub is to transmit a second signal to a cloud to determine fluctuation in the individual object.

2. The system of claim 1, wherein the control hub comprises a waterproof case to secure an electronic circuit of the control hub.

3. The system of claim 2, wherein the waterproof case includes an LED to indicate proper installation of the individual dendrometer.

4. The system of claim 1, wherein the control hub includes an antenna to transmit the second signal.

5. The system of claim 1, wherein the control hub is coupled to the plurality of dendrometers.

6. The system of claim 1, wherein the fluctuation is provided as data to a mobile application.

7. The system of claim 1, wherein the individual dendrometer includes:

a frame;

a spring;

a fork attached to the frame via the spring;

a magnet attached to end of the fork; and a magnetic sensor attached to the frame and under the magnet.

8. The system of claim 7 comprises a cable coupled to the magnetic sensor and the control hub.

9. A dendrometer comprising:

a frame;

a spring;

a fork attached to the frame via the spring;

a magnet attached to end of the fork; and a magnetic sensor attached to the frame and under the magnet.

10. The dendrometer of claim 9 includes a screw to fasten the spring to the fork.

11. The dendrometer of claim 9 including a slider coupled to two branches of the fork away from the end of the fork.

12. The dendrometer of claim 11 including at least one screw to fasten the slider to the two branches of the fork.

13. The dendrometer of claim 11, wherein the two branches of the fork include indentations to secure the slider.

14. The dendrometer of claim 9, wherein the magnetic sensor is fastened to the frame via at least one screw.

15. The dendrometer of claim 9, wherein the frame includes a joint or elbow configured to couple an object via a clamp.

16. A dendrometer comprising:

a magnetic sensor to detect displacement of a magnet on a fork, wherein the fork includes two branches that are separated by a gap large enough to hold an object.

17. The dendrometer of claim 16, wherein the magnetic sensor is to detect linear motion of the magnet by sensing changes in a magnetic field.

18. The dendrometer of claim 16, wherein the magnetic sensor includes an interface to couple to a control hub.

19. The dendrometer of claim 16 including:

a frame; and a spring coupled to the fork, wherein the magnet is attached to end of the fork, and wherein the magnetic sensor is attached to the frame and under the magnet.

20. The dendrometer of claim 16, wherein the two branches of the fork include indentations to secure a slider.

* * * * *